United States Patent [19]
Komi

[11] Patent Number: 5,569,162
[45] Date of Patent: Oct. 29, 1996

[54] STRUCTURE OF END PORTION OF SIDE-LOOKING TYPE ELECTRONIC ENDOSCOPE

[75] Inventor: Shuji Komi, Omiya, Japan

[73] Assignee: Fuji Photo Optical Co. Ltd., Omiya, Japan

[21] Appl. No.: 520,365

[22] Filed: Aug. 28, 1995

[30] Foreign Application Priority Data

Sep. 1, 1994 [JP] Japan .................................. 6-232020
Sep. 1, 1994 [JP] Japan .................................. 6-232021

[51] Int. Cl.$^6$ ...................................................... A61B 1/00
[52] U.S. Cl. ........................... 600/130; 600/170; 600/129
[58] Field of Search ............................ 600/109, 129–30, 600/160, 164, 170, 172, 175

[56] References Cited

U.S. PATENT DOCUMENTS

| | | | |
|---|---|---|---|
| 4,622,954 | 11/1986 | Arakawa et al. | 600/130 |
| 4,779,130 | 10/1988 | Yabe | 600/172 X |
| 4,787,370 | 11/1988 | Karamori | 600/182 X |
| 4,868,644 | 9/1989 | Yabe et al. | 600/109 X |
| 4,941,457 | 7/1990 | Hasegawa | 600/182 X |
| 5,325,847 | 7/1994 | Matsuno | 600/109 |

FOREIGN PATENT DOCUMENTS 25969  4/1981  European Pat. Off. ............... 600/182

Primary Examiner—Stephen R. Crow
Assistant Examiner—David R. Risley
Attorney, Agent, or Firm—Ronald R. Snider

[57] ABSTRACT

A structure of the end portion of a side-looking type electronic endoscope in which an irradiation window is disposed closer to the end than an observation window, thereby enabling a better observation of a deceased part at the time of treatment. The structure also facilitates the removal of a light guide. The observation window is disposed on the side surface of the endoscope, and a solid-state image sensor is attached to the observation window via the objective system member and the rectangular prism. A light guide is disposed in the space formed on the back side of the prism; and an irradiation window which is connected to the light guide is disposed closer to the end of the end portion than the observation window. It is therefore possible to observe the internal body as an object of inspection with the light irradiated from the portion closer to the end than the observation window. By providing a tool engaging portion which engages with a toll for removing the light guide at the end portion of the light guide, the removal of the light guide at the time of repair or replacement is facilitated.

5 Claims, 6 Drawing Sheets

FIG. 7
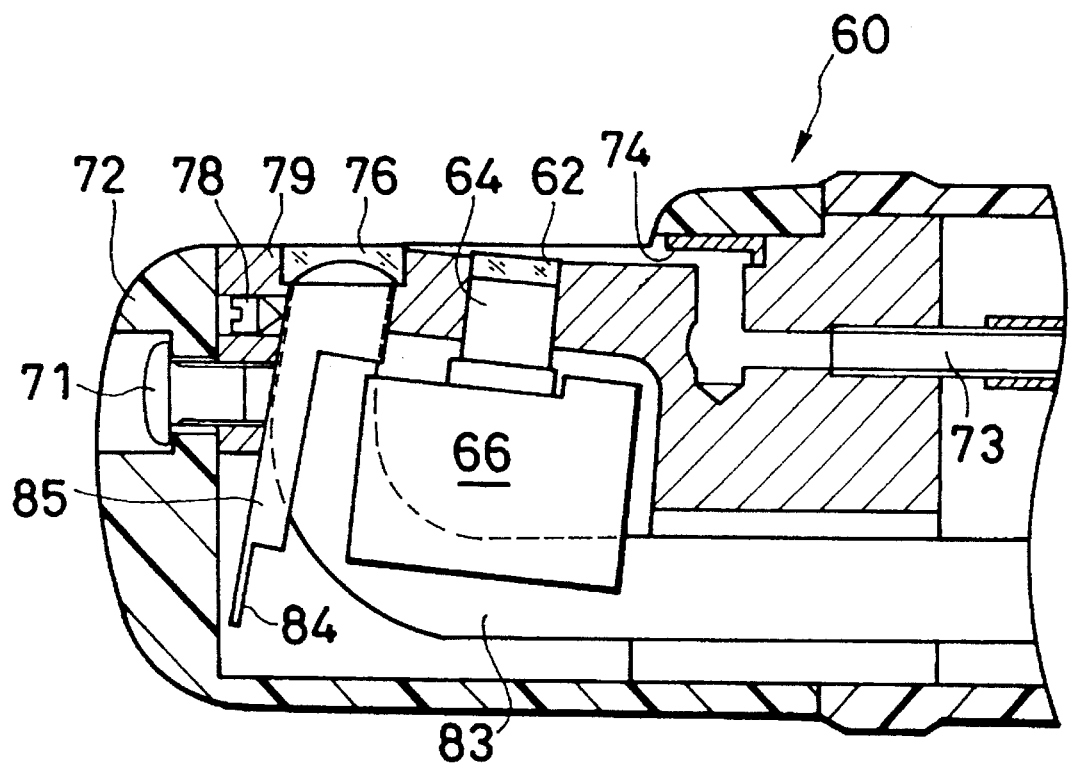
FIG.8(A)    FIG.8 (B)
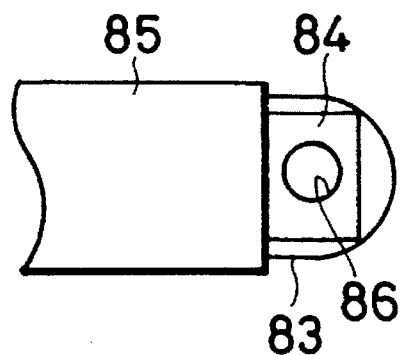    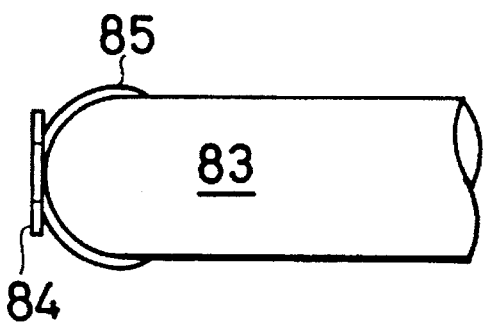

STRUCTURE OF END PORTION OF SIDE-LOOKING TYPE ELECTRONIC ENDOSCOPE

BACKGROUND OF THE INVENTION

This application claims the priority of Japanese Patent Application Nos. 6-232021 and 6-232020 filed on Sep. 1, 1994.

1. Field of the Invention

The present invention relates to a structure of the end portion of a side-looking type electronic endoscope which is provided with an irradiation window, an observation window and a forceps insertion hole arranged on the side surface thereof.

2. Description of the Related Art

FIGS. 9 and 10 show the structure of the end portion of a conventional side-looking type electronic endoscope. An observation window 2 and an irradiation window 3 are arranged on the side surface of the end portion 1 of the endoscope. A CCD (Charge Coupled Device) 5 is attached to the observation window 2 via an optical system member 4, and a signal cable 7 is connected to the printed circuit board 6 of the CCD 5. The signal cable 7 is led to, for example, an external processor apparatus. A light guide 8 is attached to the irradiation window 3. The light guide 8 is finally connected to a light source device. A raising table 10 connected to a wire 9 and supported by a shaft 11 is disposed in parallel with the observation window 2, as shown in FIG. 10, and a forceps insertion hole is provided behind the raising table 10. By raising the raising table 10 by pulling the wire 9, it is possible to lead a manipulating tool 12 from the side surface (through the forceps insertion hole) up to a predetermined position or in a predetermined direction, as shown in FIG. 9.

According to this structure of the end portion 1, the light supplied through the light guide 8 is projected into the body as the object of inspection through the irradiation window 3, and the image of the internal body is caught by the CCD 5 via the observation window 2 and the optical system member 4. The picture signals obtained by the CCD 5 are input to the external processor device or the like through the signal cable 7 and processed by the external processor device. As a result, the image of the internal body is displayed on a monitor. At the same time, it is possible to lead the manipulating tool 12 from the side surface of the end portion 1 so as to execute various treatments.

In a conventional side-looking type electronic endoscope, since the observation window 2 is disposed closer to the end than the irradiation window 3, there is a problem that a shadow is cast on the surface (an inclined surface or the like) of a protruding or recessed portion within the body which faces in the direction of insertion of the endoscope, or that the surface is shaded. For example, in the case of the mammilation of the duodenum, which is a representative part treated by an endoscope, the endoscope 14 is inserted into the duodenum 16 through the stomach 15, so as to conduct a predetermined treatment on the mammilation 19 having an opening portion which opens into the bile duct 17 and the ductus pancreaticus 18, as shown in FIG. 11. However, since the mammilation 19 is a protruding portion, as shown in FIG. 11, when light is projected from the irradiation window 3 disposed at the rear portion, the opening portion of the mammilation 19 is shaded, and it is difficult to treat the opening portion with the manipulating tool 12.

The same problem is produced in the observation of a diverticulum. In many cases, it is more convenient to dispose the irradiation window 3 closer to the end than the observation window 2. In order to dispose the irradiation window 3 closer to the end than the observation window 2, it is also necessary to dispose the light guide 8 in the vicinity of the end, which inconveniently increases the diameter of the endoscope. That is, as is clear from FIG. 10, since the optical system member 4, the CCD 5, the printed circuit board 6, the signal cable, 7, etc. are connected to the observation window 2, there is no place to dispose the light guide 8 in the state shown in FIG. 10, so that it is necessary to increase the diameter of the endoscope. However, an endoscope is required to have as small a diameter as possible in order to alleviate the pain of a patient.

In addition, in a conventional endoscope, when the printed circuit board or the like as well as the CCD is replaced, it is sometimes necessary to remove the light guide depending upon the structure of the end portion. However, since the endoscope adopts an airtight structure, the light guide is tightly adhered to the supporting portion with an adhesive or the like. It takes much time to remove the light guide, and the light guide itself is sometimes broken.

SUMMARY OF THE INVENTION

Accordingly, it is an object of the present invention to eliminate the above-described problems in the related art and to provide a structure of the end portion of a side-looking type electronic endoscope in which an irradiation window is disposed closer to the end than an observation window without increasing the diameter of the endoscope, thereby enabling a better observation of a deceased part at the time of treatment.

It is another object of the present invention to provide a structure of the end portion of a side-looking type electronic endoscope which enables a light guide to be removed easily and in a short time and which can prevent a breakage of the light guide itself.

To achieve these ends, in one aspect of the present invention, there is provided a structure of the end portion of a side-looking type electronic endoscope comprising: an observation window disposed on the side surface of the endoscope; an objective system member connected to the observation window; a prism (rectangular prism) for reflecting incident light which passes the objective system member at an approximately right angle so as to emit the light to the side surface of the endoscope; a solid-state image sensor attached to the observation window via the prism so as to pick up an image of the internal body as an object of inspection; a light guide disposed closer to the end of the end portion by utilizing the space formed on the back side of the prism; and an irradiation window which is connected to the light guide and disposed closer to the end than the observation window.

According to this structure, the solid-state image sensor, the printed circuit board and the like which are disposed at a position on which incident light directly impinges in a conventional structure are rotated at 90 degrees around the prism, so that a space is formed on the back side of the prism. By utilizing this space on the back side of the prism, the light guide is disposed between the back surface of the prism and the case body of the endoscope. By optically connecting the irradiation window to the light guide, it is possible to dispose the irradiation window closer to the end of the endoscope than the observation window.

In a structure of the end portion of a side-looking type electronic endoscope provided in another aspect of the present invention, a tool engaging member with which a removing tool engages is provided on the outer periphery of the end portion of the light guide so as to remove the light guide disposed at the end of the endoscope. This structure facilitates the removal of the light guide. It is possible to fix the light guide to the vicinity of the observation window by a screw.

A projecting portion as the tool engaging portion may be formed as the tool engaging member on a cylindrical body placed over the outer peripheral portion of the light guide. The tool engaging member may be provided with an engaging hole for receiving a hook-shaped tool.

The above and other objects, features and advantages of the present invention will become clear from the following description of the preferred embodiments thereof, taken in conjunction with the accompanying drawings.

BRIEF DESCRIPTION OF THE DRAWINGS

FIG. 7 is a sectional view of the side surface of the end portion of a third embodiment of a side-looking type electronic endoscope according to the present invention;

FIG. 8 shows the structure of the engaging member in the first embodiment, wherein FIG. 8(A) is an elevational view and FIG. 8(B) is a bottom view thereof:

DESCRIPTION OF THE PREFERRED EMBODIMENTS

First embodiment

Figure 1:
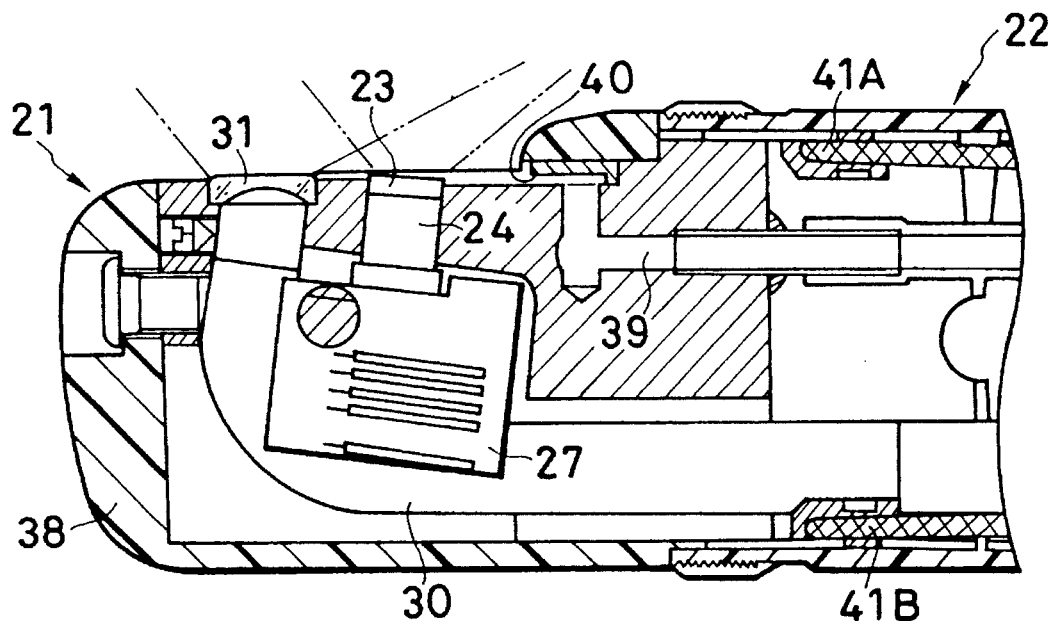
FIG. 1 is a sectional view of the side surface of the end portion of a first embodiment of a side-looking type electronic endoscope.
Figure 2:
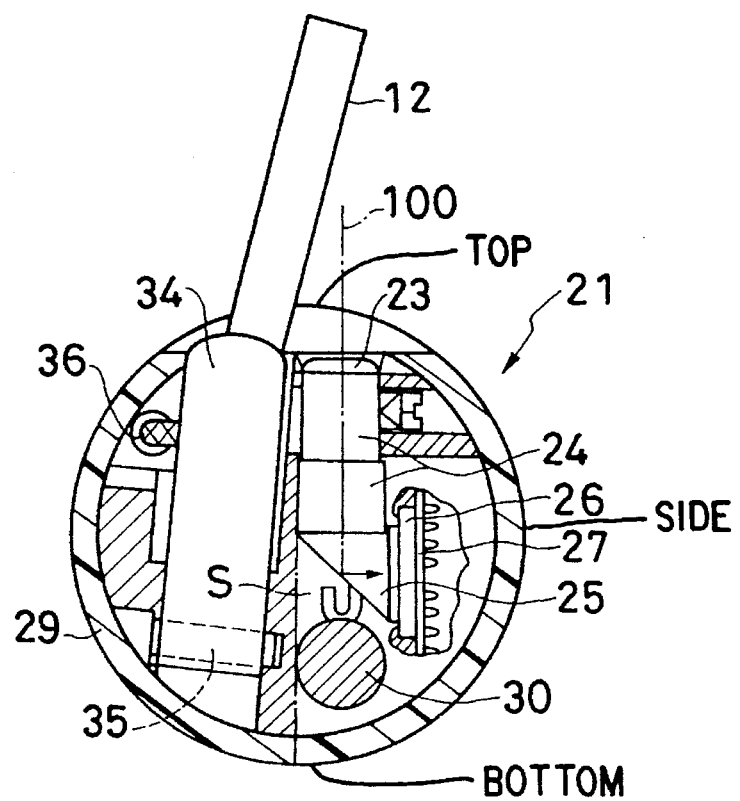
FIG. 2 is a cross sectional view of the end portion of the first embodiment shown in FIG. 1.
Figure 3:
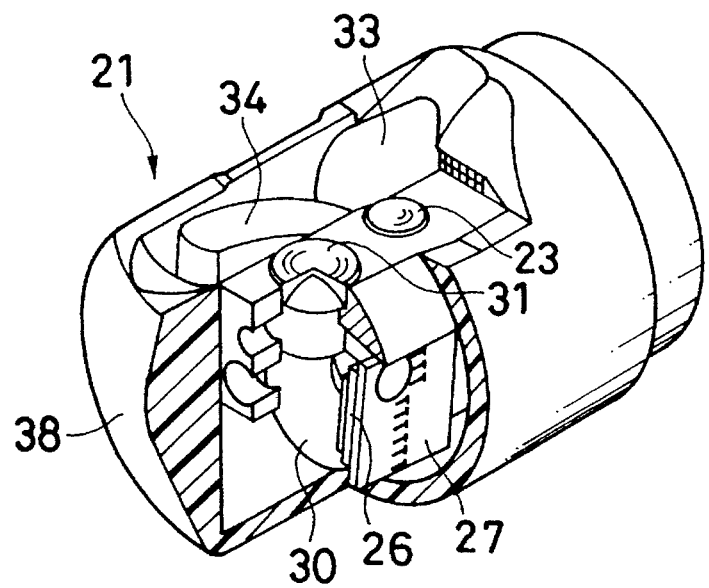
FIG. 3 is a partially sectional perspective view of the end portion of the first embodiment shown in FIG. 1, showing the light guide accommodated therein.

FIGS. 1 to 3 show the structure of the end portion of a first embodiment of a side-looking type electronic endoscope according to the present invention. An end portion 21 of the endoscope is connected to an angle portion 22. An observation window 23 is formed on the top side surface of the end portion 21, and a prism (rectangular prism) 25 is connected to the observation window 23 via an objective system 24. The prism 25 is disposed in such a manner as to reflect incident light 100 at 90 degrees and emit it toward the side surface, as shown in FIG. 2. A CCD 26 having a cover glass and a printed circuit board 27 are attached to the prism 25. In this case, the CCD 26 and the printed circuit board 27 are therefore disposed at a right angle to the side surface on which the observation window 23 and the like are disposed (rotated at 90 degrees around the observation window 23), and the pickup surface of the CCD 26 is parallel to the optical axis of the objective system 24.

At this time, a space S is formed on the back side of the prism 25, as shown in FIG. 2. In this embodiment, a light guide (a bundle of optical fibers) 30 is disposed at the bottom side between the back diagonal surface of the prism 25 and a bottom surface of said end portion and a cap 29 by utilizing this space S. An irradiation window 31 is disposed closer to the end than the observation window 23, and the light guide 30 is connected to the irradiation window 31, as shown in FIG. 1. By utilizing the observation window 23 and the irradiation window 31 which is disposed closer to the end than the observation window 23, it is possible to closely observe the surface (inclined surface, etc.) of a protruding or recessed portion within the body which faces in the direction of insertion of the endoscope. In this embodiment, a light shielding agent is applied to the outer periphery of the light guide 30 (or the light guide is accommodated in a light shielding pipe), and a light shielding agent is also applied to the outer peripheries of the prism 25 and the CCD 26 so as to exclude the influence of other light on the observation window 23 and the irradiation window 31.

A forceps insertion hole 33 which communicates with a manipulating tool channel is formed in the side surface of the end portion 21, and a raising table 34 is attached to the end of the forceps insertion hole 33, as shown in FIG. 3. The raising table 34 is supported by a shaft 35 (FIG. 2), and a wire 36 is attached to the raising table 34. When the wire 36 is pulled, the raising table 34 is raised so as to enable a manipulating tool 12 to be led out of the side surface of the end portion 21 in the perpendicular direction. A cap 38 is placed over the end portion 21, a nozzle 40 connected to an air/water supply pipe is disposed in the vicinity of the observation window 23, and wires 41A, 41B for bending the angle portion 23 are provided at the rear portion of the end potion 21, as shown in FIG. 1.

Figure 4:
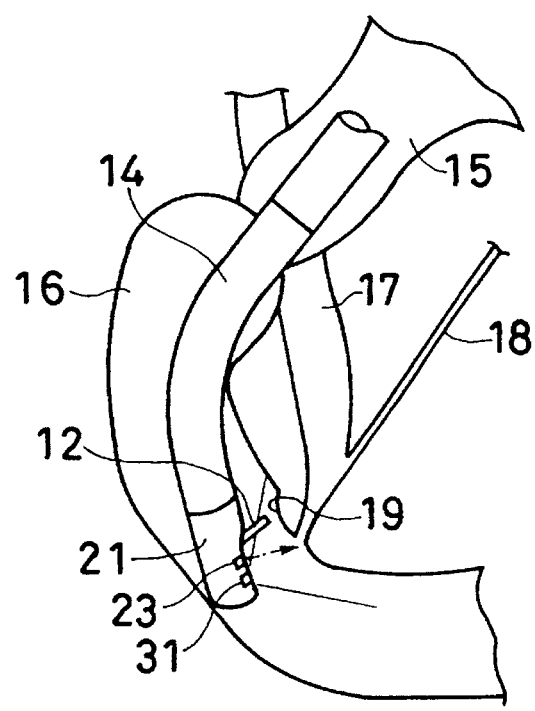
FIG. 4 shows the first embodiment applied to the mammilation of a duodenum.

FIG. 4 shows the first embodiment having the above-described structure which is applied to the mammilation of a duodenum. In the end portion 21 of the endoscope 14 which is inserted from the stomach 15 to the duodenum 16, since irradiating light is emitted from the irradiation window 31 which is disposed closer to the end than the observation window 23, it is possible to clearly irradiate the opening portion which opens into the bile duct 17 and the ductus pancreaticus 18 on the back side of the mammilation 21. It is therefore easy to treat the diseased part with the manipulating tool 12 while observing the image of the mammilation 21 which is obtained through the observation window 23.

In the first embodiment, since the prism 25 is used, the CCD 26 and the printed circuit board 27 are disposed on the side surface of the prism 25 in parallel to the optical axis, and the light guide 30 is disposed in the space S on the back side of the prism 25 adjacent to bottom surface, it is possible to dispose the light guide 30 and the irradiation window 31 closer to the end than the observation window 23 without the need for increasing the diameter of the end portion 21. As a result, it is easy to observe the surface of a protruding or recessed portion within the body which faces in the direction of insertion of the endoscope 14 by the irradiation of light through the irradiation window 31, which advantageously enables a good treatment of, for example, the mammilation 21 of the duodenum 16.

Second embodiment

Figure 5:
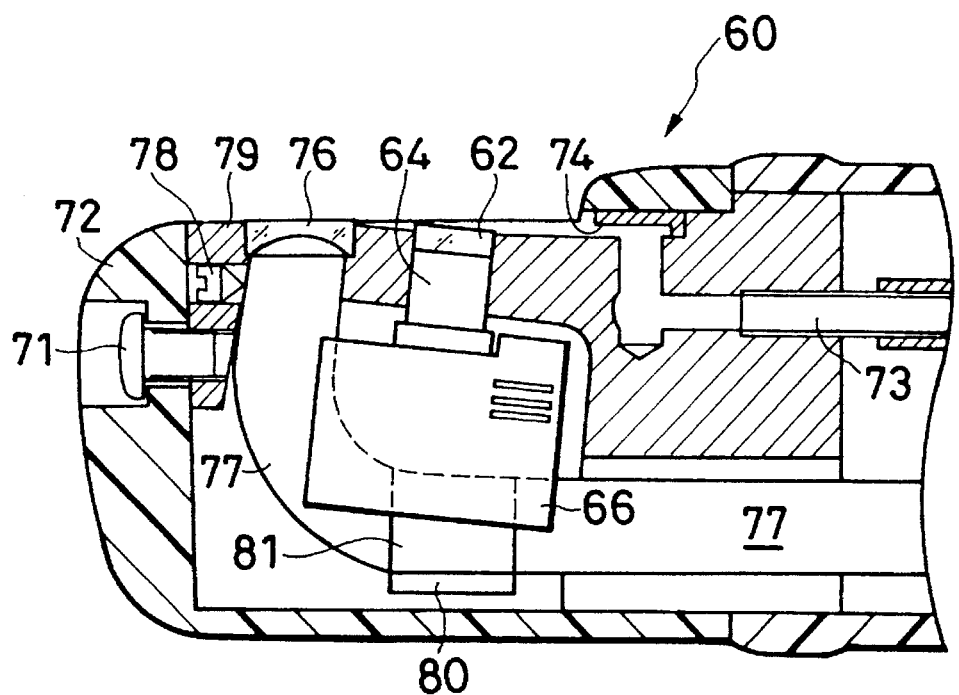
FIG. 5 is a sectional view of the side surface of the end portion of a second embodiment of a side-looking type electronic endoscope according to the present invention.
Figure 6:
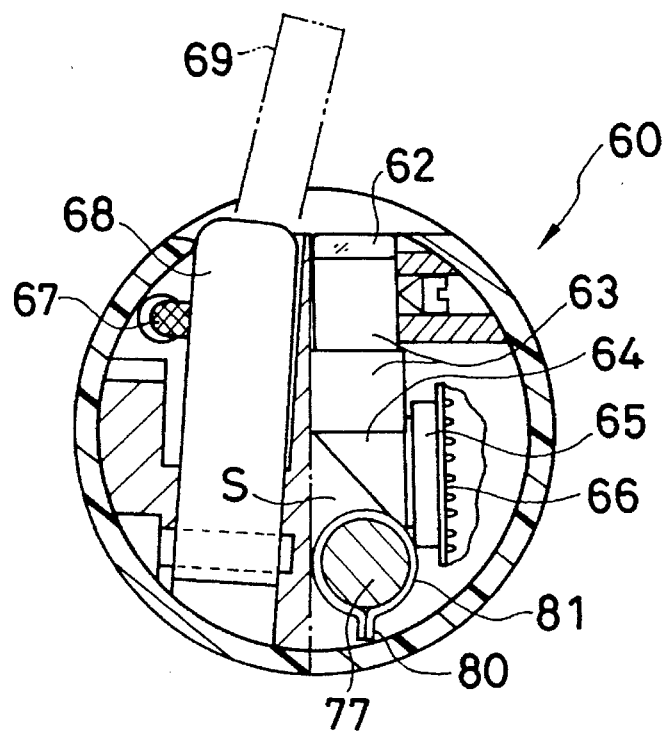
FIG. 6 is a cross sectional view of the end portion of the second embodiment shown in FIG. 5.
Figure 9:
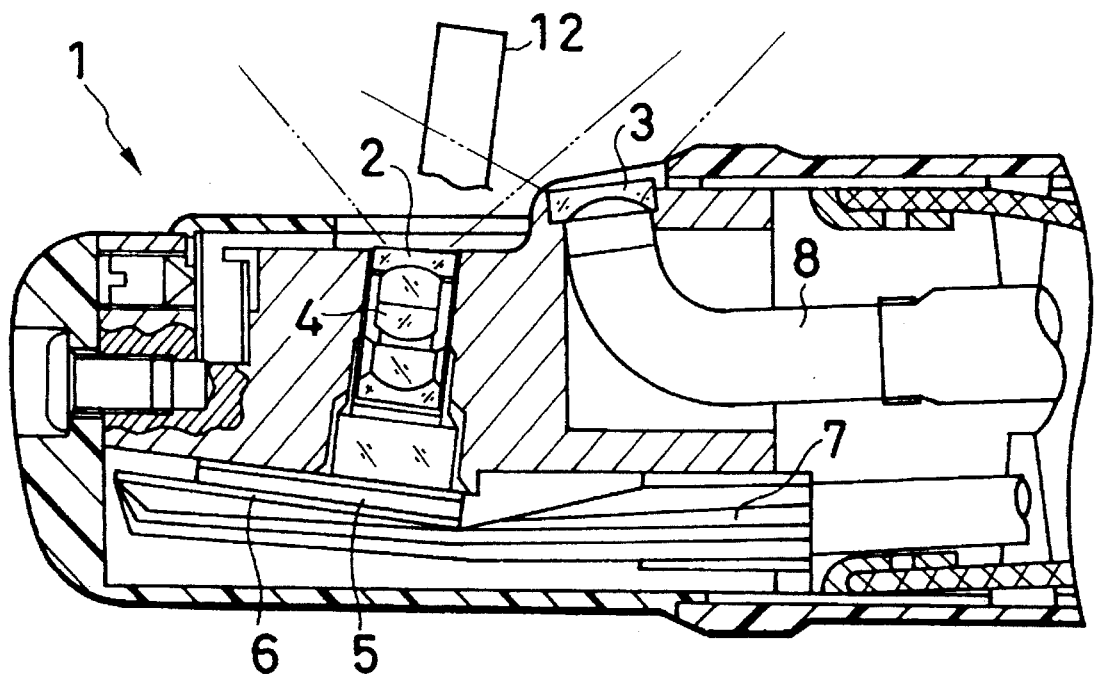
FIG. 9 is a sectional view of the side surface of the end portion of a conventional side-looking type electronic endoscope.
Figure 10:
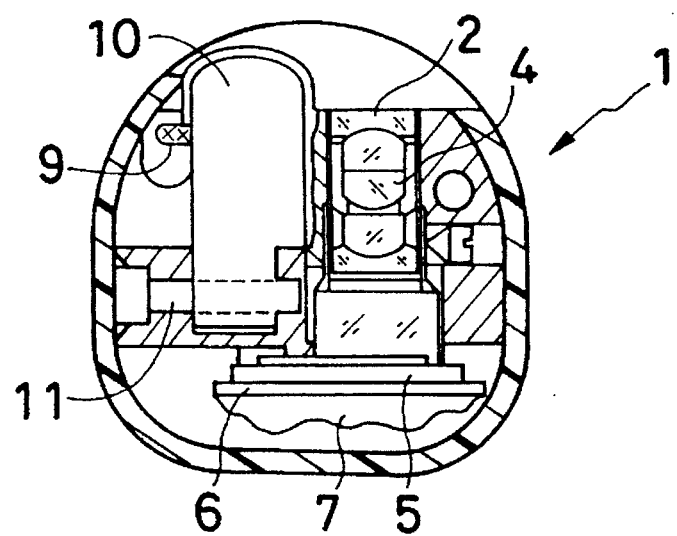
FIG. 10 is a cross sectional view of the end portion of the conventional endoscope shown in FIG. 9.
Figure 11:
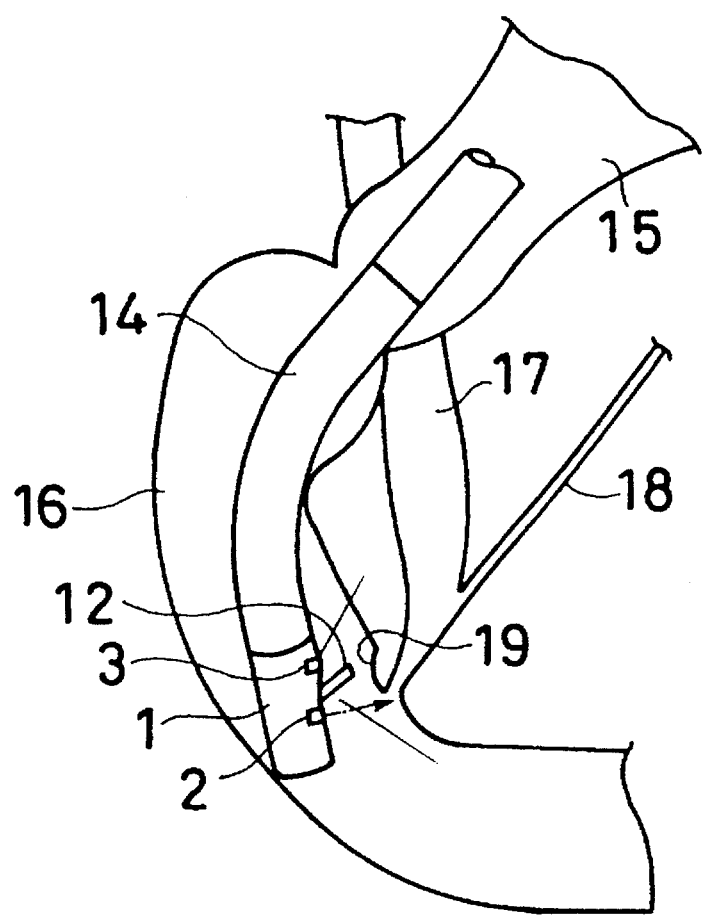
FIG. 11 shows the conventional endoscope shown in FIG. 9 applied to the mammilation of a duodenum.

FIGS. 5 and 6 show the structure of the end portion of a second embodiment of a side-looking type electronic endoscope according to the present invention. An observation window 62 is formed on the side surface of the end portion 60, and a CCD 65 is connected to the observation window 62 via an objective system 63 and a prism 64 (FIG. 6). A printed circuit board 66 is attached to the CCD 65. On the opposite side surface to the side surface on which the optical observing system members are provided, a raising table 68 to which a wire 67 is connected is provided, as shown in FIG. 6, and a forceps insertion hole for leading out a manipulating tool 69 is disposed on the back side of the raising table 68. A cap 72 fixed by a fixing screw 71 is placed over the end portion 50, and a nozzle 74 connected to an air/water supply pipe 73 is provided in the vicinity of the observation window 62, as shown in FIG. 5.

An irradiation window 76 is provided in approximately parallel with the observation window 62, and a light guide 77 consisting of a bundle of optical fibers is attached to the irradiation window 76. The outer periphery of the light guide 77 is covered with a protective pipe or a light shielding pipe. The light guide 77 is fixed to a supporting portion 79 by a predetermined set screw, and at the time of fixing the light guide 77, a sealing agent is poured so as to keep the airtightness. In this embodiment, by attaching the light guide 77 to the supporting portion 79 by using the set screw 78, it is possible to dispense with a conventional adhesive or to reduce the amount of adhesive used to a small one, which facilitates the removal of the light guide 77.

In the second embodiment, the light guide 77 is provided with a cylindrical body 81 having a small strip-like protruding portion 80 as an engaging member. The cylindrical body 81 is formed by bending a single sheet in such a manner as to leave the protruding portion 80. It is possible to engage a tool for removing the light guide 77 with the the protruding portion 80. In this case, the protruding portion is clamped by pliers or cutting pliers.

According to the second embodiment of a side-looking type electronic endoscope having the above-described structure, when the CCD 65, the printed circuit board 66 or the like is replaced, or the light guide 77 itself is replaced, the cap 72 is first removed, and the set screw 78 is then removed. Thereafter, the protruding portion 80 is clamped and pulled by a tool such as pliers and cutting pliers. In this manner, it is possible to remove the light guide 77 easily and in a short time.

In the present invention, since the irradiation window 76 is disposed closer to the end than the observation window 62 and the light guide is disposed in the space S on the back side of the prism 64, it is necessary to remove the light guide 77 when the printed circuit board 66 or the like is removed. According to the second embodiment, replacement of the printed circuit board 66 or the like is facilitated.

In the light guide 77 in a conventional endoscope, a bundle of optical fibers are disposed with the end portions bound in a bundle because it is necessary to reduce the diameter of the end portion 60. When a protective pipe or the like is provided, the pipe is made thinner at the end portion 60. As a result, when the light guide 77 is removed with a tool or the like, the light guide 77 itself is sometimes broken. In addition, when the light guide 77 is broken in the middle, a part of it is sometimes left in the hole of the supporting portion 79 for receiving the light guide 77. In such a case, since the light guide 77 is firmly adhered to the supporting portion 60 in a conventional structure, it is necessary to break the irradiation window 76, which costs much.

In the second embodiment, however, since the cylindrical body 81 having the protruding portion 80 is provided and the light guide is fixed by the set screw 78, the possibility of a breakage of the light guide 77 itself is reduced.

Third embodiment

FIGS. 7 and 8 show the structure of the end portion of a third embodiment of a side-looking type electronic endoscope according to the present invention. The arrangement of a light guide 83 and the main structure of the other portion are the same as in the second embodiment. In the third embodiment, a cylindrical body 85 having a protruding portion 84 is provided at the end of the light guide 83 as an engaging member. The cylindrical portion at the end portion is fixed to the light guide 83, and the protruding portion 84 is formed by cutting off about ¾ of the width cylinder via a middle portion formed by cutting off about more than ½ of the width of the cylinder. An engaging hole 86 is formed in the protruding portion 34, as shown in FIG. 8 (A).

According to the third embodiment, the light guide 83 is easily removed from the supporting portion 79 by clamping and pulling the protruding portion with a tool or by engaging a hook-shaped tool with the engaging hole 86 and pulling the light guide 83 after the cap 72 and the set screw 78 are removed. Breakage of the optical fibers is therefore prevented and it is not necessary to break the irradiation window 76.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A side-looking electronic endoscope comprising:

an observation window disposed on a top surface of an end portion of said endoscope;

an objective system member connected to said observation window;

a rectangular prism disposed with rectangular prism side surfaces parallel to said top surface of said end portion and a side surface of said end portion for reflecting light which passes through said objective system member at an approximately right angle so as to emit said light towards said side surface of said end portion whereby a space is provided between a diagonal back surface of said rectangular prism and a bottom surface of said end portion;

a solid-state image sensor attached to said observation window via said rectangular prism for picking up an image of the internal body as an object of inspection;

a light guide disposed between said objective system and a forward end of said end portion and passing through said space formed between said diagonal back surface of said rectangular prism and said bottom surface of said end portion; and an irradiation window which is connected to said light guide and disposed between said forward end and said observation window.

2. A side-looking electronic endoscope according to claim 1, further comprising a tool engaging portion with which a tool for removing said light guide from said forward end portion engages, and which is provided on the outer periphery of said light guide at the forward end portion thereof.

3. A side-looking electronic endoscope according to claim 2, wherein said light guide is fixed to the vicinity of said irradiation window by a screw.

4. A side-looking electronic endoscope according to claim 2, wherein said tool engaging portion is a protruding portion of a cylindrical body which is fitted over the outer periphery of said light guide.

5. A side-looking electronic endoscope according to claim 2, wherein said tool engaging portion is provided with an engaging hole for receiving a hook-shaped tool.

* * * * *